US012603151B2

(12) United States Patent
Zhang et al.

(10) Patent No.: US 12,603,151 B2
(45) Date of Patent: Apr. 14, 2026

(54) METHODS OF DESIGNING AND PREDICTING PROTEINS

(71) Applicant: The Florida State University Research Foundation, Inc., Tallahassee, FL (US)

(72) Inventors: Jinfeng Zhang, Tallahassee, FL (US); Yuan Zhang, Tallahassee, FL (US); Wei Wu, Tallahassee, FL (US); Xiuwen Liu, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 924 days.

(21) Appl. No.: 16/936,634

(22) Filed: Jul. 23, 2020

(65) Prior Publication Data

US 2021/0027860 A1 Jan. 28, 2021

Related U.S. Application Data

(60) Provisional application No. 62/877,557, filed on Jul. 23, 2019.

(51) Int. Cl.
| | |
|---|---|
| *G16B 30/00* | (2019.01) |
| *G06F 30/27* | (2020.01) |
| *G16B 15/20* | (2019.01) |
| *G16B 40/30* | (2019.01) |

(52) U.S. Cl.
CPC ............. *G16B 30/00* (2019.02); *G06F 30/27* (2020.01); *G16B 15/20* (2019.02); *G16B 40/30* (2019.02)

(58) Field of Classification Search
CPC ........ G16B 30/00; G16B 15/20; G16B 40/30; G16B 40/20; G06F 30/27
See application file for complete search history.

(56) References Cited

PUBLICATIONS

Torng, Wen, and Russ B. Altman. "3D deep convolutional neural networks for amino acid environment similarity analysis." BMC bioinformatics 18 (2017): 1-23. (Year: 2017).*
Wang, Jingxue, et al. "Computational protein design with deep learning neural networks." Scientific reports 8.1 (2018): 1-9. (Year: 2018).*

(Continued)

*Primary Examiner* — Renee D Chavez
*Assistant Examiner* — Pursottam Giri
(74) *Attorney, Agent, or Firm* — Eversheds Sutherland (US) LLP

(57) ABSTRACT

Methods of predicting or designing a protein. The methods may include providing a protein that includes a target residue; centering a gridded box on a selected atom of the target residue; collecting local structural information adjacent the selected atom and the target residue; and determining the target residue of the protein based on the local structural information. The methods may include providing a nine-layer three-dimensional deep convolutional neural network (CNN) configured to accept as input data a gridded box comprising atomic coordinates and types adjacent a target residue; and analyzing the gridded box centered on the target residue with the three-dimensional deep convolutional neural network to determine the target residue.

10 Claims, 11 Drawing Sheets

BBO

BBS

Cα-Cβ: 1.521 Å
N-C-Cα: 110.4°
N-C-Cα-Cβ: 122.55°

(56)          References Cited

PUBLICATIONS

Hendlich, Manfred, Friedrich Rippmann, and Gerhard Barnickel. "LIGSITE: automatic and efficient detection of potential small molecule-binding sites in proteins." Journal of Molecular Graphics and Modelling 15.6 (1997): 359-363. (Year: 1997).*

Pu, Limeng, et al. "Deep Drug3D: classification of ligand-binding pockets in proteins with a convolutional neural network." PLoS computational biology 15.2 (2019): e1006718. (Year: 2019).*

Carugo, Oliviero. "Wolumes—An algorithm to compute the volume of atoms and residues in proteins." arXiv preprint arXiv:1406.3242 (2014). (Year: 2014).*

Tubert-Brohman, Ivan, et al. "Improved docking of polypeptides with Glide." Journal of chemical information and modeling 53.7 ( 2013): 1689-1699. (Year: 2013).*

Li, Lishuang, Yang Liu, and Meiyue Qin. "Extracting biomedical events with parallel multi-pooling convolutional neural networks." IEEE/ACM transactions on computational biology and bioinformatics 17.2 (2018): 599-607. (Year: 2018).*

Fang et al. ("MUFOLD-SS: New deep inception-inside-inception networks for protein secondary structure prediction." Proteins: Structure, Function, and Bioinformatics 86.5 (2018): 592-598. (Year: 2018).*

Li, Zhixiu, et al. "Direct prediction of profiles of sequences compatible with a protein structure by neural networks with fragment-based local and energy-based nonlocal profiles." Proteins: Structure, Function, and Bioinformatics 82.10 (2014): 2565-2573. (Year: 2014).*

Cun, Y. Le, et al. (2000). Handwritten Digit Recognition with a Back-Propagation Network, AT&T Bell Laboratories, 396-404.

Dahiyat, B. et al. (1997). Communication; De Novo Protein Design: Towards Fully Automated Sequence Selection. 273 ESJMOB 4 789-796.

Dai L. et al. (2010). Improving Computational Protein Design By Using Structure-Derived Sequence Profile. Proteins, Structure, Function, Bioformatics, Wiley-Liss, Inc. 78:2338-2348.

Dantas, G. et al. (2003). A Large Scale Test of Computational Protein Design: Folding and Stability of Nine Completely Redesigned Globular. Proteins, Journal of Molecular Biology 332(2), 449-460.

Desjarlais, J.R. et al. (1995). De Nova Design of The Hydrophobic Cores of Proteins. Protein Science 4:2006-2018.

Faraggi, E. et al. (2012). Improving Protein Secondary Structure Prediction By Multi Step Learning Coupled With Prediction of Solvent Accessible Surface Area and Backbone Torsion Angles. Wiley Periodicals, Inc., J. Comput Chem 33: 259-267.

Goodsell, D.S. et al. (2015). The Rcsb Pdb "Molecule of the Month": Inspiring a Molecular View of Biology. PLoS Biology, 13(5), e1002140.

Krizhevsky, A. et al. (2017). Image Net Classification with Deep Convolutional Neural Networks. Communications of the ACM, 60(6), 84-90.

Li, Z., et al. (2014). Direct Prediction of Profiles of Sequences Compatible With a Protein Structure By Neural Networks With Fragment-Based Local And Energy-Based Nonlocal Profiles. Wiley Periodicals, Inc., Proteins 82:2565 2573.

O'connell, J et al. (2018). SPIN2: Predicting sequence profiles from protein structures using deep neural networks. Proteins 86:629-633.

Privett, H.K. et al. (2012). Iterative Approach to Computational Enzyme Design. Proceedings of the National Academy of Sciences of the United States of America, 109(10), 3790-3795.

Raha, K. et al. (2000). Prediction of Amino Acid Sequence From Structure. Protein Sci. 9(6):1106-1119.

Siegel, J. et al. (2010). Computational Design of An Enzyme Catalyst For a Stereoselective Bimolecular Diels—Alder Reaction. Science, 329(5989), 309-313.

Tegge, A. et al. (2009). NNcon: Improved protein contact map prediction using 2D-recursive neural networks. Nucleic Acids Research, 2009, vol. 37, Web Server issue W515-W518.

Tian, K. et al. (2016). Boosting Compound-Protein Interaction Prediction By Deep Learning. Methods (San Diego, Calif.), 110, 64-72.

Tsai, H.H. et al. (2004). In Silico Protein Design By Combinatorial Assembly of Protein Building Blocks. Protein Sci. Oct. 2004; 13(10):2753-2765.

Wang, S. et al. (2017). Accurate De Novo Prediction of Protein Contact Map by Ultra-Deep Learning Model. PLoS Comput Biol. Jan. 5, 2017;13(1):e1005324:1-34.

Wang, J. et al. (2018). Computational Protein Design with Deep Learning Neural Networks. Scientific Reports 8:6349 (9 pages).

Yin, H. et al. (2007). Computational Design of Peptides That Target Transmembrane Helices. Science, 315(5820), 1817-1822.

* cited by examiner

Cα-Cβ: 1.521 Å
N-C-Cα: 110.4°
N-C-Cα-Cβ: 122.55°

BBO

BBS

FIG. 4A

BBO30  IKEGSPEIRALGAKIAAL LEKAVEHVDNLPPALAPLAVEVSHVLKIP

BBO90  LSEGSPVLALGAKIGETIRKAVAHIDNPEPALADESEGVSNVLKIP

BB530  LSKGSPTVRALGAKIAALGRAVANIDNLPPALADLISNVLKIP

BB590  LSRGSPQVKALGKVADTLRKAVAHIDNLPSALADLIANVLKIP

True    LSHGSAQVKGHGKKVADALTNAVAHVDDMPNALSALSDLHAHKLRVD

FIG. 4B

BBO30

BBO90

BBS30

BBS90

True   PVNFKLLSHCLLVTLAAHLPAEFTPAVHASLDKFLASVSTVLTSKYR

FIG. 4C

Confusion Matrix

Color scale: 0.9  0.8  0.7  0.6  0.5  0.4  0.3  0.2  0.1

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4187 | 2178 | 1096 | 2487 | 656 | 459 | 9521 | 2977 | 510 | 883 | 4173 | 3437 | 275 | 905 | 1880 | 4140 | 1702 | 135 | 815 | 3356 |
| R | 3027 | 11019 | 1584 | 1553 | 68 | 942 | 7549 | 991 | 585 | 1029 | 3852 | 6910 | 113 | 433 | 887 | 1549 | 2196 | 79 | 902 | 2723 |
| N | 1998 | 1336 | 14004 | 7827 | 265 | 314 | 4406 | 2072 | 940 | 318 | 1431 | 1500 | 74 | 387 | 719 | 1656 | 1422 | 60 | 691 | 1128 |
| D | 3116 | 1097 | 14608 | 25964 | 215 | 285 | 9912 | 2014 | 656 | 336 | 1440 | 1910 | 46 | 361 | 1605 | 2618 | 1410 | 82 | 683 | 1008 |
| C | 2676 | 276 | 379 | 381 | 4514 | 102 | 376 | 509 | 166 | 267 | 862 | 189 | 121 | 284 | 175 | 530 | 555 | 29 | 227 | 1293 |
| Q | 2340 | 2754 | 1260 | 1745 | 77 | 4260 | 9101 | 931 | 413 | 692 | 3071 | 4299 | 208 | 257 | 577 | 1087 | 1548 | 63 | 434 | 1816 |
| E | 2263 | 376 | 786 | 1011 | 159 | 131 | 1627 | 66578 | 142 | 105 | 732 | 412 | 53 | 160 | 664 | 1196 | 481 | 38 | 167 | 331 |
| G | 1270 | 1177 | 1516 | 1468 | 96 | 230 | 2081 | 705 | 4732 | 380 | 1697 | 1320 | 60 | 976 | 358 | 761 | 767 | 199 | 1973 | 1004 |
| H | 858 | 688 | 142 | 301 | 63 | 148 | 1564 | 163 | 127 | 2241 | 6628 | 968 | 159 | 682 | 310 | 224 | 1159 | 83 | 502 | 16242 |
| I | 2428 | 2065 | 587 | 847 | 151 | 490 | 3899 | 733 | 428 | 5764 | 56323 | 2453 | 420 | 2243 | 675 | 581 | 1266 | 175 | 1460 | 5061 |
| L | 3284 | 5780 | 1632 | 2114 | 38 | 1100 | 1182 | 1171 | 555 | 841 | 3449 | 14673 | 119 | 239 | 1129 | 1677 | 2301 | 74 | 680 | 2671 |
| K | 1833 | 765 | 315 | 401 | 121 | 378 | 1304 | 396 | 170 | 1122 | 5494 | 634 | 1488 | 507 | 227 | 415 | 706 | 43 | 360 | 1701 |
| M | 1512 | 748 | 508 | 658 | 104 | 87 | 1290 | 462 | 754 | 1180 | 5452 | 551 | 83 | 15148 | 326 | 470 | 701 | 418 | 1705 | 1931 |
| F | 1512 | 748 | 508 | 658 | 104 | 87 | 1290 | 462 | 754 | 1180 | 5452 | 551 | 83 | 15148 | 326 | 470 | 701 | 418 | 1705 | 1931 |
| P | 655 | 118 | 65 | 353 | 26 | 26 | 580 | 375 | 32 | 60 | 267 | 144 | 21 | 73 | 43254 | 410 | 72 | 18 | 43 | 160 |
| S | 9018 | 1540 | 1987 | 3492 | 405 | 390 | 7090 | 2782 | 497 | 319 | 1559 | 2289 | 130 | 414 | 1627 | 2240 | 5807 | 83 | 702 | 1540 |
| T | 2665 | 1638 | 833 | 1745 | 330 | 405 | 5553 | 911 | 358 | 1214 | 2471 | 2670 | 166 | 477 | 748 | 3547 | 25307 | 66 | 664 | 5660 |
| W | 754 | 433 | 217 | 444 | 54 | 44 | 804 | 242 | 559 | 428 | 1926 | 288 | 41 | 1731 | 211 | 319 | 313 | 3633 | 2407 | 757 |
| Y | 1266 | 832 | 706 | 855 | 81 | 99 | 1617 | 494 | 1062 | 822 | 3639 | 727 | 62 | 6236 | 353 | 596 | 720 | 451 | 4245 | 1603 |
| V | 1740 | 1046 | 270 | 489 | 163 | 213 | 2936 | 260 | 217 | 9660 | 5275 | 1591 | 140 | 794 | 550 | 402 | 2342 | 82 | 719 | 42514 |

FIG. 5

BLOSUM62

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -3 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -1 | -3 | 1 | 0 | -1 | -2 | -3 |
| D | -2 | -2 | 1 | 0 | -3 | 0 | 2 | -1 | -1 | -3 | -4 | -1 | -3 | -3 | -1 | 0 | -1 | -4 | -3 | -3 |
| C | 0 | -3 | -3 | -3 | 2 | -3 | -4 | -3 | -3 | -1 | -1 | -3 | -1 | -2 | -1 | -1 | -1 | -2 | -2 | -1 |
| G | -1 | 1 | 0 | 0 | -3 | 6 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| Q | 0 | -2 | 0 | -1 | -3 | -3 | -2 | 6 | -2 | -1 | -1 | -2 | -3 | -3 | -3 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -1 | -3 | -4 | -3 | 4 | 2 | -3 | 1 | 0 | -1 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 6 | 0 | -2 | -1 | -1 | -1 | -1 | 1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -1 | 7 | -1 | -1 | -1 | -3 | -2 |
| S | 1 | -1 | 1 | 0 | -1 | 0 | 0 | 0 | -1 | -2 | -2 | 0 | -1 | -2 | -1 | 4 | 1 | -2 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |
| W | -3 | -3 | 4 | 4 | -2 | -2 | -3 | -2 | -2 | -3 | -2 | -3 | -1 | 1 | -4 | -1 | -2 | 11 | 2 | -3 |
| Y | -2 | -2 | -2 | -3 | -2 | -1 | 2 | -3 | 2 | -1 | -1 | -2 | -1 | 3 | -3 | -2 | -2 | 2 | 7 | -1 |
| V | 0 | -1 | -3 | -3 | -3 | -1 | -2 | -3 | -3 | 3 | 1 | -2 | 1 | -1 | -2 | -2 | 0 | -3 | -1 | 4 |

FIG. 6A

BBO_ID90

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 10 | -8 | -6 | -3 | 1 | -6 | 1 | -6 | -5 | -9 | -6 | -2 | -4 | -6 | -7 | 1 | -6 | -8 | -6 | -6 |
| R | -3 | 0 | -2 | -5 | -2 | -1 | 2 | -10 | -2 | -5 | -2 | 5 | -5 | -7 | -11 | -4 | -2 | -3 | -4 | -4 |
| N | -5 | -2 | 12 | 6 | -1 | -5 | 0 | -6 | 1 | -14 | -0 | -2 | -0 | -8 | -13 | -2 | -6 | -10 | -5 | -10 |
| D | -3 | -5 | 5 | 12 | -5 | -7 | 3 | -7 | -2 | -13 | -9 | -3 | -12 | -2 | -8 | -1 | -5 | -2 | -8 | -10 |
| C | 1 | -0 | -1 | -6 | 10 | -10 | -6 | -6 | -12 | -6 | -11 | -0 | 0 | -6 | -13 | -1 | -1 | -10 | -6 | -5 |
| G | -6 | -1 | -6 | -7 | -10 | 7 | 2 | -12 | -6 | -11 | -0 | 0 | -6 | -13 | -10 | -8 | -0 | -14 | -11 | -8 |
| E | 1 | 2 | 0 | 3 | -2 | 2 | -11 | -6 | -2 | -5 | -3 | 5 | -6 | -7 | -7 | 0 | -0 | -7 | -4 | -3 |
| Q | -6 | -10 | -0 | -7 | -8 | -12 | -0 | -14 | -10 | -20 | -13 | -10 | -13 | -14 | -11 | -0 | -11 | -16 | -13 | -17 |
| H | -5 | -2 | 1 | -2 | -5 | -8 | -2 | -10 | -13 | -10 | -5 | -2 | -3 | 0 | -13 | -5 | -5 | 0 | 3 | -1 |
| I | -0 | -6 | -14 | -13 | -10 | -11 | -6 | -20 | -10 | 12 | 2 | -7 | -6 | -5 | -17 | -15 | -6 | -0 | -6 | 7 |
| L | -5 | -2 | -8 | -2 | -7 | -5 | -3 | -13 | -2 | 2 | 11 | -3 | 0 | 0 | -13 | -10 | -6 | -5 | -2 | -1 |
| K | -2 | 5 | -2 | -3 | -13 | 0 | 5 | -10 | -2 | -7 | -3 | 0 | -0 | -10 | -11 | -0 | -1 | -10 | -6 | -1 |
| M | -4 | -0 | -0 | -12 | -4 | -5 | -0 | -13 | -8 | -5 | 0 | -8 | 8 | -7 | -10 | -0 | -7 | -11 | -0 | -0 |
| F | -5 | -7 | -0 | -2 | -7 | -13 | -7 | -14 | -0 | -5 | -0 | -10 | -7 | 13 | -14 | -10 | -0 | 2 | 0 | -5 |
| P | -7 | -11 | -13 | -8 | -13 | -16 | -7 | -11 | -13 | -17 | -10 | -11 | -16 | -14 | 17 | -8 | -14 | -14 | -16 | -14 |
| S | 1 | -6 | -2 | -1 | -4 | -5 | 0 | -6 | -5 | -10 | -10 | -3 | -2 | -10 | -5 | 10 | 1 | -11 | -7 | -10 |
| T | -5 | -2 | -5 | -5 | -1 | -6 | 0 | -11 | -5 | -6 | -6 | -1 | -7 | -8 | -11 | 1 | 12 | -11 | -6 | -1 |
| W | -5 | -6 | -10 | -8 | -10 | -14 | -1 | -15 | 0 | -0 | -5 | -10 | -11 | 2 | -14 | -11 | -11 | 18 | 3 | -9 |
| Y | -6 | -4 | -6 | -6 | -8 | -11 | -8 | -12 | 3 | -6 | -2 | -6 | -9 | 8 | -15 | -7 | -6 | 3 | 14 | -5 |
| V | -5 | -4 | -10 | -10 | -5 | -8 | -3 | -17 | -7 | 7 | -1 | -4 | -8 | -5 | -14 | -10 | -1 | -9 | -5 | 12 |

METHODS OF DESIGNING AND PREDICTING PROTEINS

CROSS-REFERENCE TO RELATED APPLICATIONS

This application claims priority to U.S. Provisional Patent Application No. 62/877,557 filed Jul. 23, 2019, which is incorporated herein by reference.

STATEMENT REGARDING FEDERALLY SPONSORED RESEARCH OR DEVELOPMENT

This invention was made with government support under Contract No. R01GM126558 awarded by the National Institutes of Health (NIH). The government has certain rights in this invention.

BACKGROUND

As "machines of life", proteins can play one or more important roles in cellular processes, such as transcription, translation, signaling, cell cycle control, etc. Computational protein design (CPD) is a technique by which proteins are computationally designed to have a specific structure and/or function(s). Significant progress in computational protein design has been made in the last few decades, including progress in enzyme design, and membrane protein design.

There can be one or more different sub-problems that afflict CPD. For example, the inverse protein folding (IPF) problem is the problem of finding the amino acid sequences that fold into a known three-dimensional (3D) structure. Addressing this problem has the potential to improve the fundamental understanding of the sequence-structure relationship of proteins.

As a further example, another potential problem includes designing proteins with new functions, such as enzyme design. The design usually starts from a known structure, which is kept in the process, and then part of the sequence can be modified to achieve a new function. Variations of this problem can include specificity design and/or affinity design, where the function(s) of designed proteins are not new, but some properties of functions are the target of CPD.

The third type of CPD may include changing one or more chemical and/or physical properties of the proteins, such as increasing the stability of the designed proteins. Increasing the thermostability of enzymes can be useful in the manufacturing industry, where enzymes are used for the production of chemicals.

There have been some successes regarding IPF in the past. The agreement between the predicted sequences and the native sequence of each backbone template has ranged from 24% to 28% on four protein superfamily motifs: SH3 domain, the homeodomain (HM), the fibronectin type III (FNIII) domain, and the RNA recognition motif (RRM).

Calculating the sequence identity to the wild-type (or native) sequence or the recovery rate of the native sequence for a given structure is a common assessment method for the designed sequences. The average sequence recovery achieved by the current top-performing protein-design program is approximately 35% on a small number of proteins.

The number of protein sequences and structures in the Protein Data Bank (PDB) has grown significantly in recent years. The increase of data allows more complex models to be built for protein design. In the past decade, research in deep neural networks (DNNs or deep learning methods) has made very rapid progress and provided solutions to many problems, such as image recognition, speech recognition, and natural language processing by training complex models using very large volumes of training data. Unlike conventional machine learning techniques that require a feature extraction step that transforms the raw data into a suitable representation as the input, deep neural networks can allow raw data to be fed directly to a network with certain architecture.

In deep learning, more efforts are made in selecting the type of DNNs and designing specific architecture for the selected DNN framework. In the last few years, deep learning has been applied in computational studies of protein structures, such as protein secondary structure predictions (see, e.g., Faraggi, E. et al. (2012) SPINE X: Improving protein secondary structure prediction by multistep learning coupled with prediction of solvent accessible surface area and backbone torsion angles. J. Comput. Chem.), protein contact map prediction (see, e.g., Tegge, A. N. et al. (2009) NNcon: Improved protein contact map prediction using 2D-recursive neural networks. Nucleic Acids Res.), and protein-protein interaction predictions (see, e.g., Tian, K. et al. (2016) Boosting compound-protein interaction prediction by deep learning. Methods).

DNNs have also been used for protein design. SPIN (Sequence Profiles by Integrated Neural network) has been developed, which is based on fragment-derived sequence profiles and structure-derived energy profiles (see, e.g., Tian, K. et al. (2016) Boosting compound-protein interaction prediction by deep learning. Methods. 2016). Both local and non-local features were designed and served as input for a two hidden layer neural network which contained 51 hidden neurons and one bias. SPIN yielded an average sequence recovery of 30.7% for a dataset with 1532 proteins.

SPIN was later upgraded to SPIN2 with more local features including two more backbone angles as well as more non-local features, such as contact numbers. This network included three hidden layers with 500 sigmoid nodes each. The output layer had 20 SoftMax nodes representing the 20 types of amino acid residues. SPIN2 achieved an average sequence recovery of 34.4% for the dataset with 1532 proteins. Structural features have been used as input, such as cos and sin values of backbone dihedrals, the total solvent accessible surface area of backbone atoms, atom distances, number of hydrogen bonds and secondary structures. A multi-layer neural network was constructed including a residue probability network and a weight-network followed by several fully-connected layers, and a 20-dimensional SoftMax layer was used as the final output, but the best recovery rate was 34% on a dataset with 10173 proteins (30% sequence identity), and 38.3% on a dataset with 17607 proteins (90% sequence identity).

Among all deep learning frameworks, convolutional neural network (CNN) (Wang, S. et al. (2017) Accurate De Novo Prediction of Protein Contact Map by Ultra-Deep Learning Model. PLoS Comput. Biol.)(Cun, Y. Le et al. (2000) Handwritten Digit Recognition with a Back-Propagation Network. Integr. Vlsi J.) has been widely used, especially for object recognition.

There remains a need for methods that address one or more of the foregoing problems, including methods for predicting and/or designing proteins that fold to a 3D structure.

BRIEF SUMMARY

Provided herein are methods that address one of more of the foregoing problems. Methods are provided herein for predicting and/or designing protein sequences, including protein sequences that fold to a known 3D structure, thereby addressing the IPF problem. The IPF problem is formulated in embodiments herein as a three-dimensional object recognition problem: predicting the residue type given the three-dimensional environment, such as the backbone structure of proteins. Embodiments of the methods provided herein can also be used to predict single residue mutations that stabilize a given protein structure.

Methods of predicting or designing a protein are provided. In some embodiments, the methods include providing a protein including a target residue; centering a gridded box on a selected atom of the target residue; collecting local structural information adjacent the selected atom and/or the target residue; and determining the target residue of the protein, such as at a selected time, based on the local structural information.

In some embodiments, the methods include providing a nine-layer three-dimensional deep convolutional neural network (CNN) configured to accept as input a gridded box including atomic coordinates and types around a selected atom and/or target residue; and analyzing the gridded box centered on the target residue with the three-dimensional deep convolutional neural network to determine the target residue. The nine-layer three-dimensional deep convolutional neutral network may include (i) a layer including three parallel three dimensional convolution layers, (ii) a first max pooling layer, (iii) a three dimensional convolution layer including a plurality of channels, (iv) a second max pooling layer, (v) a flatten layer, (vi) a fully connected layer, (vii) a dropout layer, (viii) an activation layer, or (ix) a combination thereof.

Additional aspects will be set forth in part in the description which follows, and in part will be obvious from the description, or may be learned by practice of the aspects described herein, or derived from targeted research work. The advantages described herein may be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 4A, FIG. 4B, and FIG. 4C depict sequence predictions for embodiments of the methods herein.

FIG. 5 depicts a confusion matrix for an embodiment of a method herein.

FIG. 6A depicts a modified confusion matrix for an embodiment of a method performed with model BLO-SUM62.

FIG. 6B depicts a modified confusion matrix for an embodiment of a method performed with model BBO_ID90.

DETAILED DESCRIPTION

Figure 1A:
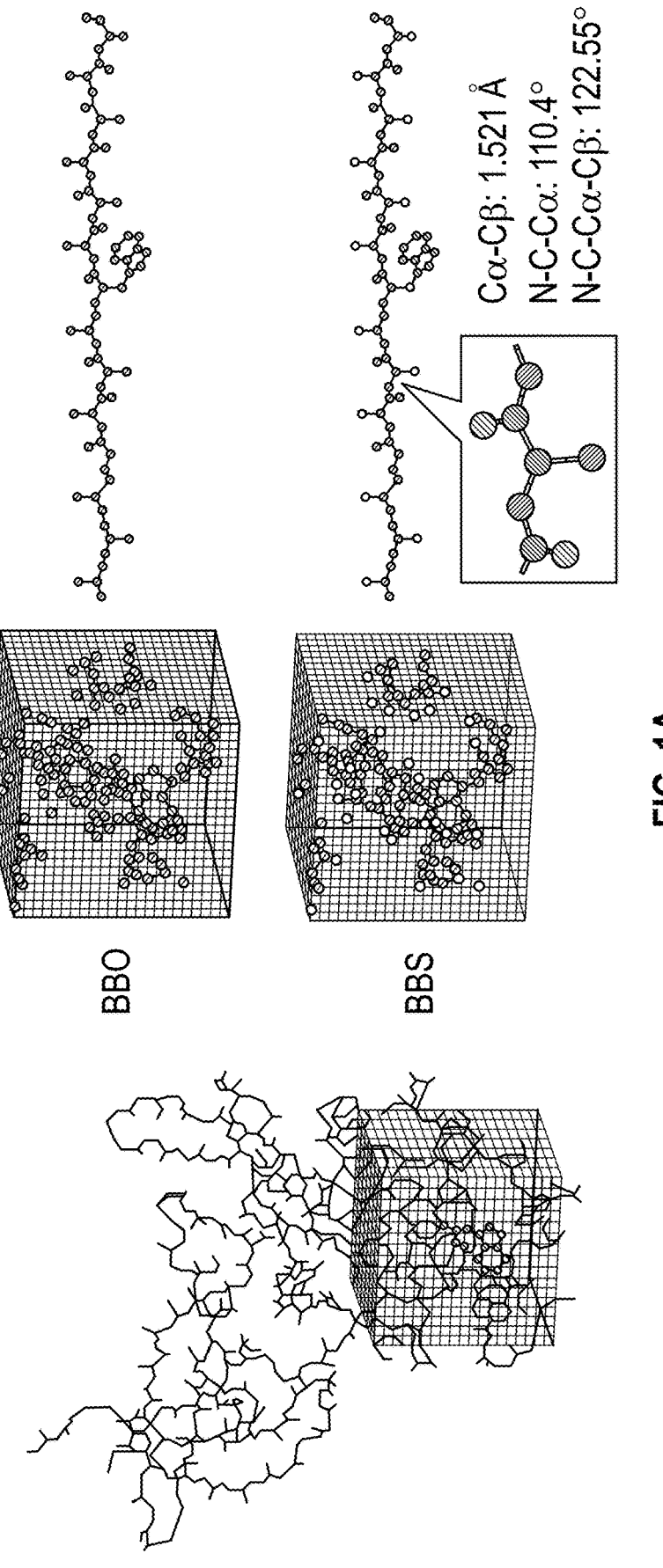
FIG. 1A depicts a snapshot of an embodiment of a gridded box, and atoms captured by the embodiment of the gridded box.

Provided herein are methods of predicting or designing a protein. In some embodiments, the methods include providing a protein including a target residue. The providing of the protein may include orienting the protein at a selected position. In some embodiments, the providing of the protein includes orienting the protein at a position at which a $C_\alpha$—C bond of the target residue aligns with or is arranged on an x-axis. In some embodiments, the providing of the protein includes orienting the protein at a position at which a $C_\alpha$—N bond of the target residue aligns with or is arranged in an x-y plane. In some embodiments, the providing of the protein includes orienting the protein at a position at which (i) a $C_\alpha$—C bond of the target residue aligns with or is arranged on an x-axis, and (ii) a $C_\alpha$—N bond of the target residue aligns with or is arranged in an x-y plane.

The target residue may be any residue of a protein. In some embodiments, the methods include centering a gridded box on a selected atom of the target residue; collecting local structural information adjacent the selected atom and/or the target residue; and determining the target residue of the protein, such as at a selected time, based on the local structural information.

Therefore, a gridded box may be centered on the residue to collect local structural information, such as the local 3D environment information. The local structural information can include the coordinates and/or types of most, if not all, the atoms in the gridded box. The structural information for determining a target residue type at a particular position on a given protein structure, in some embodiments, includes the atoms surrounding the target residue, as depicted, for example, at FIG. 1A.

In some embodiments, the methods herein include applying a backbone only model or a backbone with sequence model. The backbone only model may have a recovery rate of at least 50%, a soft recovery rate of at least 80%, or a combination thereof. The backbone with sequence model may have a recovery rate of at least 60%, a soft recovery rate of at least 85%, or a combination thereof.

In some embodiments, the determining of the target residue of the protein includes predicting the residue type given a point cloud (coordinates and/or types of all the atoms in the box). Therefore, some embodiments described herein rely on a convolutional neural network (CNN) architecture that includes three parallel layers configured to capture local protein structural features, such as bonds, angles, and/or dihedral angles, and by another layer configured to recognize the secondary structure of the proteins (see, e.g., FIG. 1B).

In some embodiments, the methods provided herein include providing a nine-layer three-dimensional deep CNN configured to accept as input a gridded box including atomic coordinates and types adjacent a target residue; and analyzing the gridded box centered on the target residue with the three-dimensional deep convolutional neural network to determine the target residue. Therefore, in some embodiments, instead of extracting structural features, the gridded box is fed directly to the CNN to learn all the parameters in the CNN model for residue type prediction. A sliding window going through the sequence may be used, which may predict each residue type one by one. Compared with SPIN and Wang's model, an embodiment of a method provided herein, called ProDCoNN (Protein Design using Convolutional Neural Networks), surprisingly achieved substantially improved performance, as explained herein.

The selected atom on which a gridded box is centered may include any atom of a target residue. In some embodiments, the selected atom of the target residue is a $C_\alpha$ atom of the target residue. Other selected atoms are envisioned.

A gridded box generally may have any size, and its size may depend on one or more structural characteristics of a protein, target residue, or a combination thereof. In some embodiments, a gridded box is a square having sides that are about 10 angstroms to about 30 angstroms in length. In some embodiments, a gridded box is a square having sides that are about 15 angstroms to about 25 angstroms in length. In some embodiments, a gridded box is a square having sides that are about 15 angstroms to about 20 angstroms in length. In some embodiments, a gridded box is a square having sides that are about 18 angstroms in length.

A gridded box may include a plurality of voxels. The plurality of voxels may include any number of voxels. In some embodiments, the gridded box includes about 4,000 to about 7,000 voxels, about 5,000 to about 6,000 voxels, or about 5,500 to about 6,000 voxels. Each voxel of the plurality of voxels may have any unit size. In some embodiments, each voxel has a unit size of about 0.1 angstrom to about 2 angstroms by about 0.1 angstrom to about 2 angstroms by 0.1 angstrom to about 2 angstroms. In some embodiments, each voxel has a unit size of about 0.5 angstrom to about 1.5 angstroms by about 0.5 angstrom to about 1.5 angstroms by 0.5 angstrom to about 1.5 angstroms.

In some embodiments, the methods provided herein include smoothing the input data, such as the data of a gridded box or local structural information. The smoothing of the input data may include applying three dimensional truncated Gaussian functions with standard deviation $\sigma_x = \sigma_y = \sigma_z = r$, wherein r is equal to ±0.5 angstrom of a Van der Waals radius of an atom in a voxel of the gridded box. The Van der Waals radius for carbon, nitrogen, and oxygen may be 0.7 angstroms, 0.65 angstroms, and 0.6 angstroms, respectively.

In some embodiments, the determining of the target residue includes providing local structural information and/or a gridded box as input to a convolutional neural network (CNN). The convolutional neural network may have an architecture that includes two or more layers, wherein the two or more layers are selected from the group consisting of (i) a layer including three parallel three dimensional convolution layers, (ii) a first max pooling layer, (iii) a three dimensional convolution layer including a plurality of channels, (iv) a second max pooling layer, (v) a flatten layer, (vi) a fully connected layer, (vii) a dropout layer, and (viii) an activation layer. In some embodiments, the nine-layer three-dimensional deep convolutional neutral network includes (i) a layer including three parallel three dimensional convolution layers, (ii) a first max pooling layer, (iii) a three dimensional convolution layer including a plurality of channels, (iv) a second max pooling layer, (v) a flatten layer, (vi)

a fully connected layer, (vii) a dropout layer, and (viii) an activation layer. The plurality of channels of the three dimensional convolution layer may include 25 to 81 channels, 36 channels to 64 channels, 49 to 64 channels, or 64 channels.

In some embodiments, the CNN includes Protein Design with Convolutional Neural Networks (ProDCoNN), as described herein.

In some embodiments, the CNN is a nine-layer three-dimensional deep convolutional neural network in which at least one of the nine layers is configured to capture structural information at one or more different scales. The one or more different scales may include bond lengths, bond angles, torsion angles, secondary structures, or a combination thereof.

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

The present disclosure may address one or more of the problems and deficiencies of known methods and processes. However, it is contemplated that various embodiments may prove useful in addressing other problems and deficiencies in a number of technical areas. Therefore, the present disclosure should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

In the descriptions provided herein, the terms "includes," "is," "containing," "having," and "comprises" are used in an open-ended fashion, and thus should be interpreted to mean "including, but not limited to." When methods or systems are claimed or described in terms of "comprising" various steps or components, the methods or systems can also "consist essentially of" or "consist of" the various steps or components, unless stated otherwise.

The terms "a," "an," and "the" are intended to include plural alternatives, e.g., at least one. For instance, the disclosure of "a target residue," "a protein," and the like, is meant to encompass one, or mixtures or combinations of more than one target residue, protein, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in some embodiments, that a gridded box is a square having sides that are about 15 angstroms to about 20 angstroms in length. This range should be interpreted as encompassing about 15 angstroms and about 20 angstroms, and further encompasses "about" each 16 angstroms, 17 angstroms, 18 angstroms, and 19 angstroms, including any ranges and sub-ranges between any of these values.

As used herein, the term "about" means plus or minus 10% of the numerical value of the number with which it is being used.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Protein Design

The method of this example addressed a protein design problem by predicting one residue, referred to herein as a target residue, at a time using the local structural information surrounding the target residue.

Figure 1B:
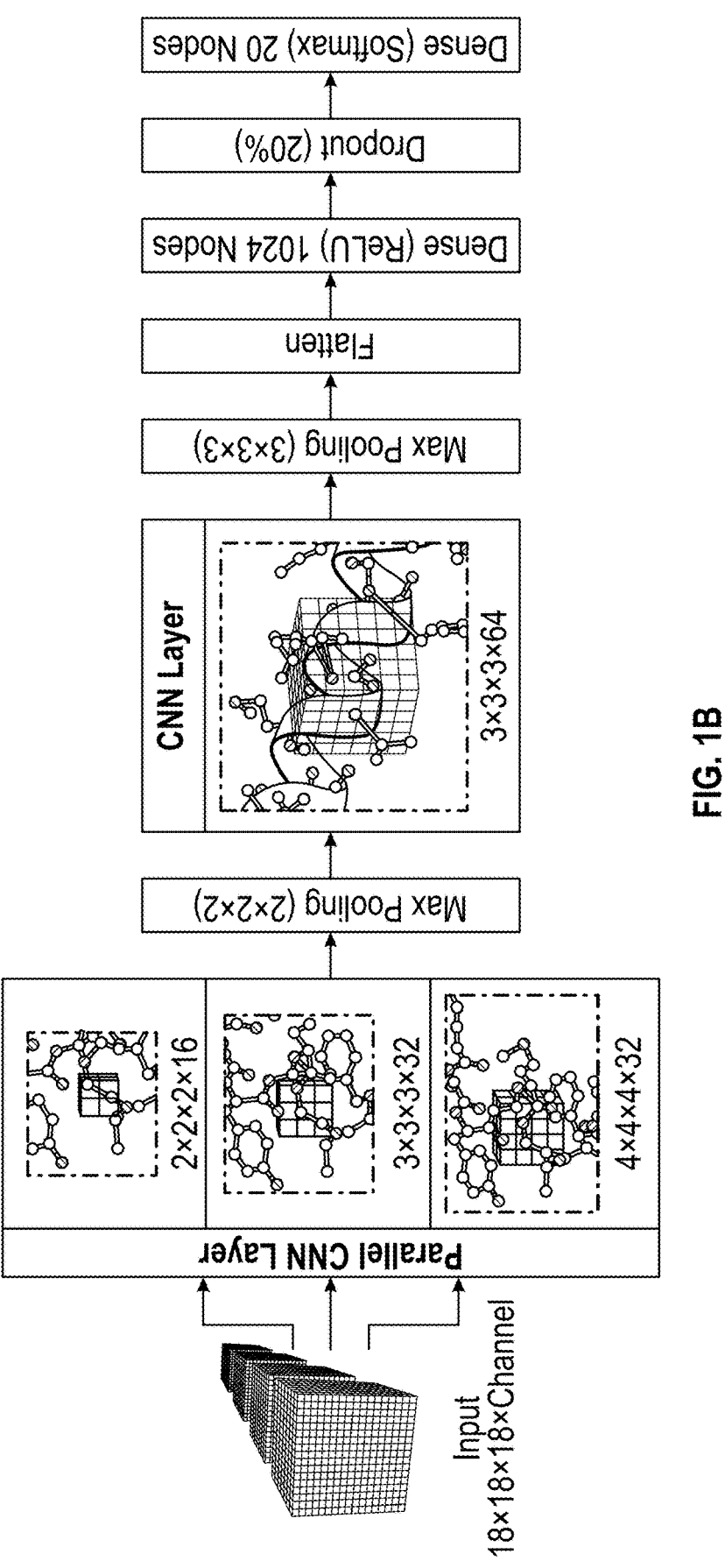
FIG. 1B depicts the architecture of an embodiment of a neural network.

A gridded box centered on the target residue was used to capture the local structural information around it, as depicted at FIG. 1A and FIG. 1B.

FIG. 1A depicts a snapshot of the gridded box, of this example, that captures the environment atoms to predict the amino acid type (black). FIG. 1A also depicts a visualization of atoms (gray) captured by the box, which used this input to make a CNN sequence prediction.

The BBO model depicted at FIG. 1A used the backbone atoms (C, Cα, N, O and the extra oxygen atom OXT on the terminal carboxyl group) and the pseudo-$C_\beta$ atom, which added manually with the bond length of $C_\alpha$—$C_\beta$ as 1.521 Å, bond angle N—C—$C_\alpha$ as 110.4°, and dihedral angle N—C—$C_\alpha$—$C_\beta$ as 122.55°.

The BBS model depicted at FIG. 1A used the same atom set but labeled $C_\beta$ (white) on non-target residues differently based on the residue type where it belonged.

FIG. 1B depicts the architecture of the Neural Network of this example. The input included an $N_{channel}$ set of 18×18× 18 gridded boxes, and each channel represented the occupation of one type of atom.

The box of this example was 18 Å on each side and centered on the $C_a$ atom of the target residue. The box was gridded with each voxel being unit size (1 Å×1 Å×1 Å). With this resolution (each box had 5832 voxels), most of the voxels contained no more than one heavy atom.

For each target residue, the protein was rotated to orient its $C_\alpha$—C bond on the '-x' axis, and its $C_\alpha$—N bond on the x-y plane. Each atom type was represented by a different channel (analogous to RGB color channels in images).

With N types of heavy atoms, the dimension of input data was 18×18×18×N. If an atom was only represented by the voxel it occupied, the exact coordinate information of the atom was lost. To overcome this limitation caused by the discretization of the 3D space around the target residue, the input data was smoothed using three dimensional truncated Gaussian functions with standard deviation $\sigma_x = \sigma_y = \sigma_z = r$, where r was the Van der Waals radius of the atom in a given voxel.

The values for the radius were 0.7 Å, 0.65 Å, and 0.6 Å for carbon, nitrogen, and oxygen, respectively. Each heavy atom was represented by a Gaussian function, whose density was spread over the voxel the atom occupied and the 26 adjacent voxels. The exact densities in each voxel were dependent on the coordinate of the atom. The side chain atom information of the target residue was removed from the input data.

In addition to keeping all the backbone atoms (C, $C_\alpha$, N and 0) and the extra oxygen atom OXT on the terminal carboxyl group, a pseudo-$C_\beta$ atom was also added to each residue including GLY. The $C_\beta$ atom at residue i had bond length for $C_\alpha^i$—$C_\beta^i$ bond as 1.521 Å, bond angle $N^i$—$C^i$—$C_\alpha^i$ as 110.4° and dihedral angle $N^i$—$C^i$—$C_\alpha^i$—$C_\beta^i$ as 122.55°.

Two models were trained for different applications: Backbone only model (BBO) took protein backbone conformation information as input which was suitable for full sequence prediction beginning with backbone structures only. Six input channels, which corresponded to atom C, $C_\alpha$, N, O, OXT and $C_\beta$ had been used for this model. Backbone with sequence model (BBS) took backbone information plus $C_\beta$ atoms of non-target residues labelled as one of the 20 amino acid types based on the sequence information. Twenty-six input channels, which corresponded to atom C, $C_a$, N, O, OXT, $C_\beta$ of target residue and 20 types of $C_\beta$ (non-target residue), had been used for BBS model. This model required sequence information except target residue, which was suitable for predicting a single residue given the backbone structure and the amino acid types of the rest of the sequence.

The sequence recovery rates by the models of this example trained on a dataset with 8,120 protein chains were 42.20% for the BBO model (see Example 2 for details) and 47.63% for the BBS model. The recovery rates of the BBO and BBS models trained on another dataset with 17,040 protein chains were 46.50% and 52.15%, respectively.

Example 2—Datasets

In this example, 10,149 protein structures (ID30) were selected with the sequence's identity lower than 30% from PDB (Rose, P. W. et al. (2017) The RCSB protein data bank: Integrative view of protein, gene and 3D structural information. Nucleic Acids Res.). All the structures were determined by X-ray crystallography with a resolution better than 2.0 Å, and did not have any DNA/RNA/UNK molecules.

Randomly picked were 90% protein chains (9,135 protein chains) as training data (ID30TR), and the rest 10% (1,014 protein chains) as test data (ID30TS). Another 50 protein chains (TS50) which were not included in the above dataset were used to test the models and compare with other methods. These 50 protein chains (pdb name+chain) were 1ahsA, 1bvyF, 1pdoA, 2va0A, 3ieyB, 2xr6A, 3ii2A, 1or4A, 2qd1A, 3nzmA, 3vjzA, 1eteA, 2a21A, 2fvvA, 314rA, 11pbA, 3nngA, 2cviA, 3gknA, 2j49A, 3fhkA, 3pivA, 31qcA, 3gfsA, 3e8 mA, 1dx5I, 3ny7A, 3k7 pA, 2cayA, 1i8 nA, 1v7 mV, 1h4aX, 3t5gB, 3q4oA, 3a4rA, 2i39A, 3aqgA, 3ejfA, 3nbkA, 4gcnA, 2xdgA, 3gwiA, 3hklA, 3so6A, 3on9A, 4dkcA, 2gu3A, 2xcjA, 1yl1A, and 1mr1C, which were used by SPIN and Wang et al.'s model to compare with other methods (Wang, S. et al. (2017) Accurate De Novo Prediction of Protein Contact Map by Ultra-Deep Learning Model. PLoS Comput. Biol.).

Also generated was another dataset ID90, which included 21,071 protein structures from PDB with sequence identity lower than 90%. All the structures were determined by X-ray crystallography with the resolution better than 2.0 Å and did not have any DNA/RNA/UNK molecules. 17,044 protein structures were used as training data (ID90TR), and the remaining 4,027 protein structures as test data (ID90TS). The sequence identity of the structures between ID90TR and ID90TS were lower than 30% if the length difference<=20%. The dataset TS50 was excluded from ID90TR. The BBO and BBS models trained on ID30TR were labeled as BBO_ID30 and BBS_ID30, and the ones trained on ID90TR were labeled as BBO_ID90 and BBS_ID90.

Example 3—Network Architecture

As depicted at FIG. 1B, the CNN architecture had, in total, nine layers, which are described in detail as follows:

First Layer: The input layer with dimension 18×18×18× $N_{channel}$. $N_{channel}$ was the number of atom types.

Second Layer: Three parallel 3D convolution layers (conv3D) with rectified linear unit (ReLU) activation function. The first of the conv3D layers applied 16 channels of 2×2×2 convolutional filters (2×2×2×16) across the input with a stride as one to generate an output feature map with the same dimension as the input. This layer was designed to capture the information of covalent bonds, whose lengths ranged from about 1.2 Å to about 1.8 Å. The second conv3D layer applied 32 channels of 3×3×3 convolutional filters (3×3×3×32) with a stride as one, which was designed to recognize bond angles formed by two connected bonds. The last conv3D layer applied 32 channels of 4×4×4 convolutional filters (4×4×4×32) with a stride as one, which was aimed to capture information on dihedral angles.

Third Layer: All the outputs in layer 2 were combined (18×18×18×80) and fed into a 2×2×2 max pooling unit to get an output of dimension 9×9×9×80. Due to the max pooling process, the grid resolution changed to 2 Å.

Fourth Layer: A conv3D layer with 64 channels of 3×3×3 filter was added to detect secondary structure motifs such as alpha helices and beta sheets.

Fifth Layer: A max pooling layer (3×3×3) was applied to get an output of (3×3×3×64).

Sixth Layer: A flatten lay to convert the output of layer 5 to a simple vector.

Seventh Layer: A fully connected layer with ReLU activation function.

Eighth Layer: A dropout layer with a drop rate of 0.2.

Ninth Layer: A 20-dimensional SoftMax activation layer was the final output, which could be interpreted as the probability of 20 amino acid types of the target residue.

The neural network was constructed using the Keras library (Dantas, G. et al. (2003) A large scale test of computational protein design: Folding and stability of nine completely redesigned globular proteins. J. Mol. Biol.).

The rectified linear unit (ReLU) was used as the activation function for all layers except the output layer where SoftMax activation function was used. Also used was the categorical cross-entropy as the loss function and Adam for optimization. The model was trained for 7, 12, 7, 13 epochs for model BBO_ID30, BBO_ID90, BBS_ID30 and BBS_ID90, respectively, with a batch size of 200 and a learning rate of 0.01. Batch normalization was used to reduce the internal covariate shift and dropout (drop rate=0.2) to reduce overfitting in the neural network.

Example 4—Overall Recovery Rate

The average overall recovery rates of the different models of the foregoing examples are shown at Table 1.

TABLE 1

The average recovery rate (%) and fuzzy recovery rate (%) based on BLOSUM62 of different neural network models (BBO, BBS) trained with dataset ID30TR and ID90TR and test on dataset ID30TS (for ID30 models), ID90TS (for ID90 models) and TS50.

| Model | BBO_ID30 | BBO_ID90 | BBS_ID30 | BBS_ID90 |
|---|---|---|---|---|
| Overall recovery rate | 42.20% | 46.50% | 47.63% | 52.15% |
| Fuzzy recovery rate | 61.43% | 64.90% | 65.79% | 69.53% |
| Recovery rate on TS50 | 38.71% | 40.69% | 43.20% | 45.58% |
| Fuzzy recovery rate on TS50 | 58.81% | 59.91% | 62.15% | 64.33% |

The overall recovery rate was defined as the percent of amino acid residues that were predicted the same as the native sequence for a given protein structure. The BBS model trained on ID90TR had the best performance with a 52.15% recovery rate on the test dataset ID90TS, and the BBS model trained on ID30TR had 47.63% recovery rate on ID30TS.

The model trained on ID90TR increased the performance by more than 4%, indicating that the performance could be improved even further with more training data. Even though the sequence identity in ID90 data set was much higher than ID30, the training data and test data was split to make sure that the sequence identity was lower than 30% between training and test dataset. So, the improvement came mainly from the increased training data size (17,044 protein chains), which was nearly doubled compared to that of ID30TR (9,135 protein chains).

All the models with the data set TS50 were tested, which was excluded from all the training data sets ID30TR and ID90TR. The recovery rates for BBO models were 40.69% and 38.71%, when trained on ID90TR and ID30TR, respectively. The performance of the methods described herein compared favorably to those of previous studies. The average recovery rate on TS50 by Wang et al.'s model, trained on a dataset with sequence identity less than 30%, was 33.0%. The average recovery rates for SPIN and SPIN2 were 30.2% and 34.4% on a 500 proteins dataset which contained TS50.

Also calculated was a fuzzy recovery rate which was defined as the percent of amino acid residues that were predicted the same as the native residue types or as a substitutable residue type corresponding to BLOSUM62 (scores from the matrix are positive). (Henikoff, S. and Henikoff, J. G. (1992) Amino acid substitution matrices from protein blocks. Proc. Natl. Acad. Sci. U.S.A) The fuzzy recovery rates for BBO models were 64.90% (BBO_ID90) and 61.43% (BBO_ID30), when trained on ID90TR and ID30TR, respectively, for BBS models were 69.53 (BBS_ID90) and 65.79% (BBS_ID30).

Example 5—Accuracy on Different Amino Acid Types

Figures 2A, 2B, 2C, 2D:
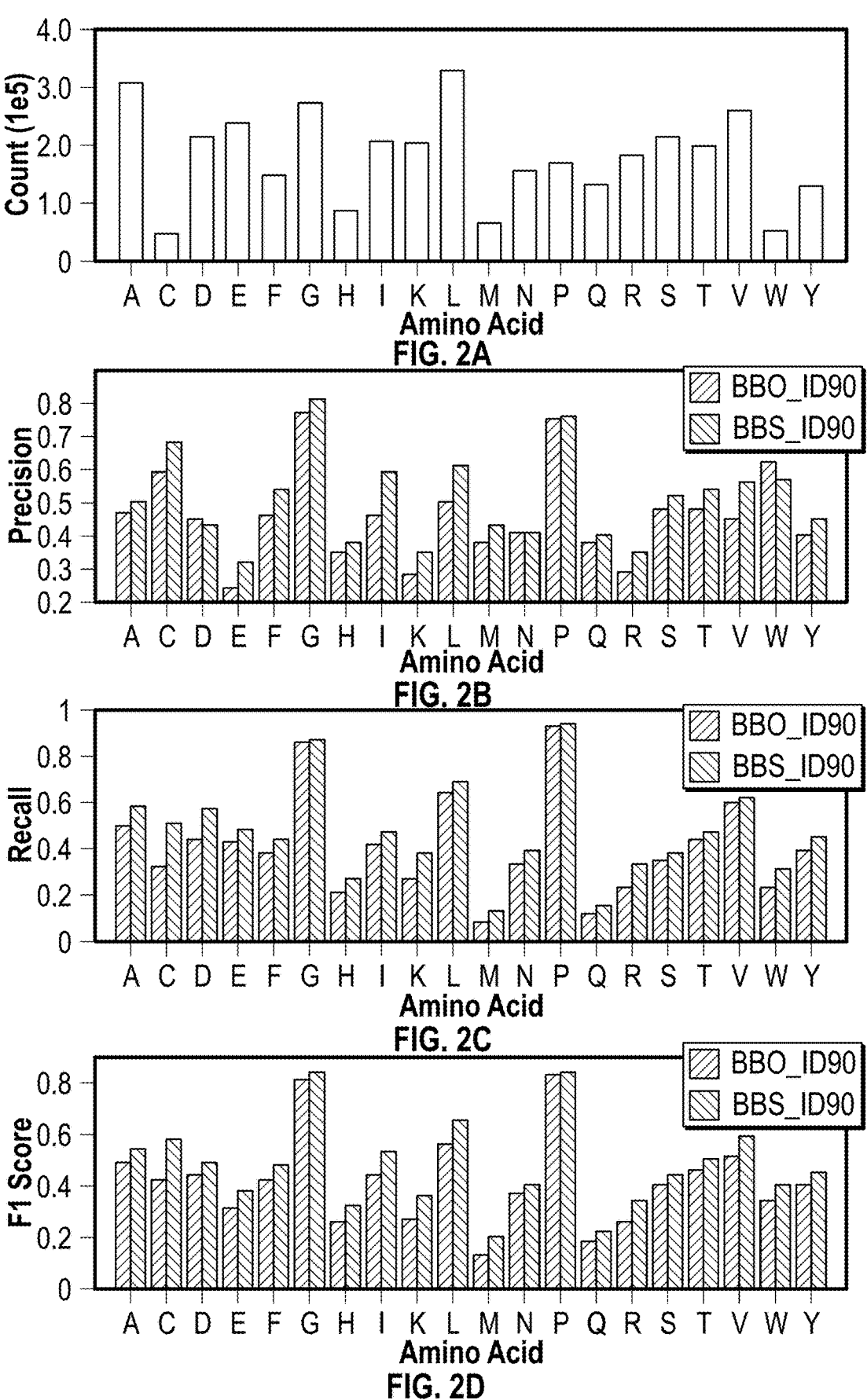
FIG. 2A depicts the count of each amino acid in an embodiment of a method.
FIG. 2B depicts the precision of different amino acids of the networks of an embodiment of a method.
FIG. 2C depicts the recall of different amino acids of the networks of an embodiment of a method.
FIG. 2D depicts the F1 score of different amino acids of the networks of an embodiment of a method.

FIG. 2A, FIG. 2B, FIG. 2C, and FIG. 2D show the distribution of each amino acid type in training data ID90TR and ID30TR, as well as the precision, recall and F1 score of BBO and BBS models trained on these datasets. Specifically, FIG. 2A depicts the count of each amino acids in ID90TR, and FIG. 2B, FIG. 2C, and FIG. 2D depicts the precision, recall, and F1 score, respectively, of different amino acids of the networks BBO and BBS trained on ID90TR.

Precision was the percent of prediction that was correct, and recall was the percent of native residue that was correctly predicted. There were large variations on the precisions and recalls among different amino acids types with GLY and PRO having the best accuracy for both models, and GLN and MET having the worst accuracy.

Example 6—Top-K Recovery Rate

Due to the fact that the last layer of the model outputs the probability of each amino acid, the top-K recovery rate could be calculated, where the prediction was considered as correct if the native residue type was within the top-K predictions based on the probabilities. As shown at FIG. 3A and FIG. 3B, the best performance was achieved by BBS_ID90 model, which gave the top-2, 3, 5, 10 recovery rates as 67.89%, 75.99%, 85.27%, and 95.60%.

Figure 3A:
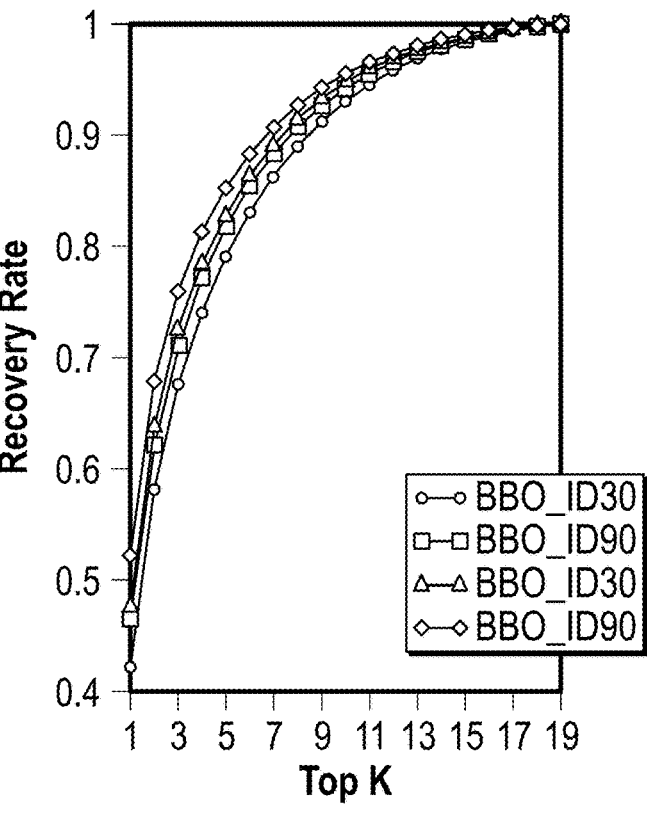
FIG. 3A depicts recovery rates for models of embodiments described herein.
Figure 3B:
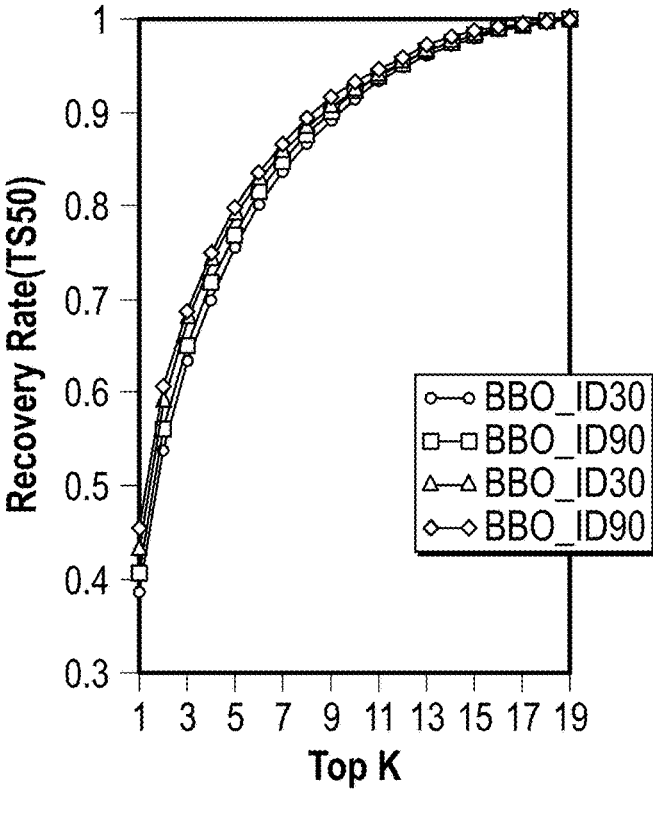
FIG. 3B depicts recovery rates for models of embodiments described herein.

FIG. 3A depicts the top-K recovery rate of models BBO_ID30, BBO_ID90, BBS_ID30, and BBS_ID90 tested on their testing data. FIG. 3B depicts the top-K recovery rates for the same models tested on TS50.

The BBO_ID30 yield topped 2, 3, 5, 10 recovery rates as 58.12%, 67.57%, 79.07% and 93.11%. The BBO_ID90 yields topped 2, 3, 5, 10 recovery rates as 62.23%, 71.13%, 81.79% and 94.32%. The fact that the top-10 predictions of the models could reach well above 90% indicated that the models described herein could separate very well those residues that may fit for a particular position in a structure and those residues that fit poorly for that position. Also calculated was the top-K recovery rate of all the models on TS50 dataset, and the best BBO model (BBO_ID90) reached 40.69%, 56.11%, 65.09%, 76.87% and 92.41% for top-1, 2, 3, 5, 10 recovery rates. Comparing with SPIN and Wang et al.'s model, which gave (30.2%, 45.3%, 55.2%, 67.7% and 86.8%) and (33.0%, 48.7%, 58.5%, 71.7% and 86.8%) for top-1, 2, 3, 5, 10 recovery rates, the model described herein made substantial improvements than SPIN and Wang et al.'s model.

Example 7—Soft Sequence Recovery Accommodating Homologous Sequences: A Case Study on Deoxy Human Hemoglobin It is well-known that proteins can undergo substantial mutations while maintaining their three-dimensional structures and stabilities. If mutated proteins were made using predicted sequences not exactly the same as native sequences, the mutants could still fold to three-dimensional structures similar to the input structure. In such cases, the predictions could still be considered satisfactory.

BBO_ID90 model was used to predict the protein sequences of deoxy human hemoglobin (pdb id: 1a3n, chain A and B), and obtained the recovery rate of 45.39% and 51.72% for 1a3 nA and 1a3nB, respectively. Although it has been suggested that native sequences are optimal for their structures, highly similar structures can still have significantly different sequences.

Used herein was FATCAT (Flexible structure AlignmenT by Chaining Aligned fragment pairs allowing Twists) (Kuhlman, B. and Baker, D. (2000) Native protein sequences are close to optimal for their structures. Proc. Natl. Acad. Sci.) server to get all the sequences (77 protein chains for 1a3 nA and 77 protein chains for 1a3nB) whose corresponding structures were similar to 1a3 nA and 1a3nB using cutoff values of 0 for both p-value (very small p-values are rounded to zero) and twist.

Figure 4A:
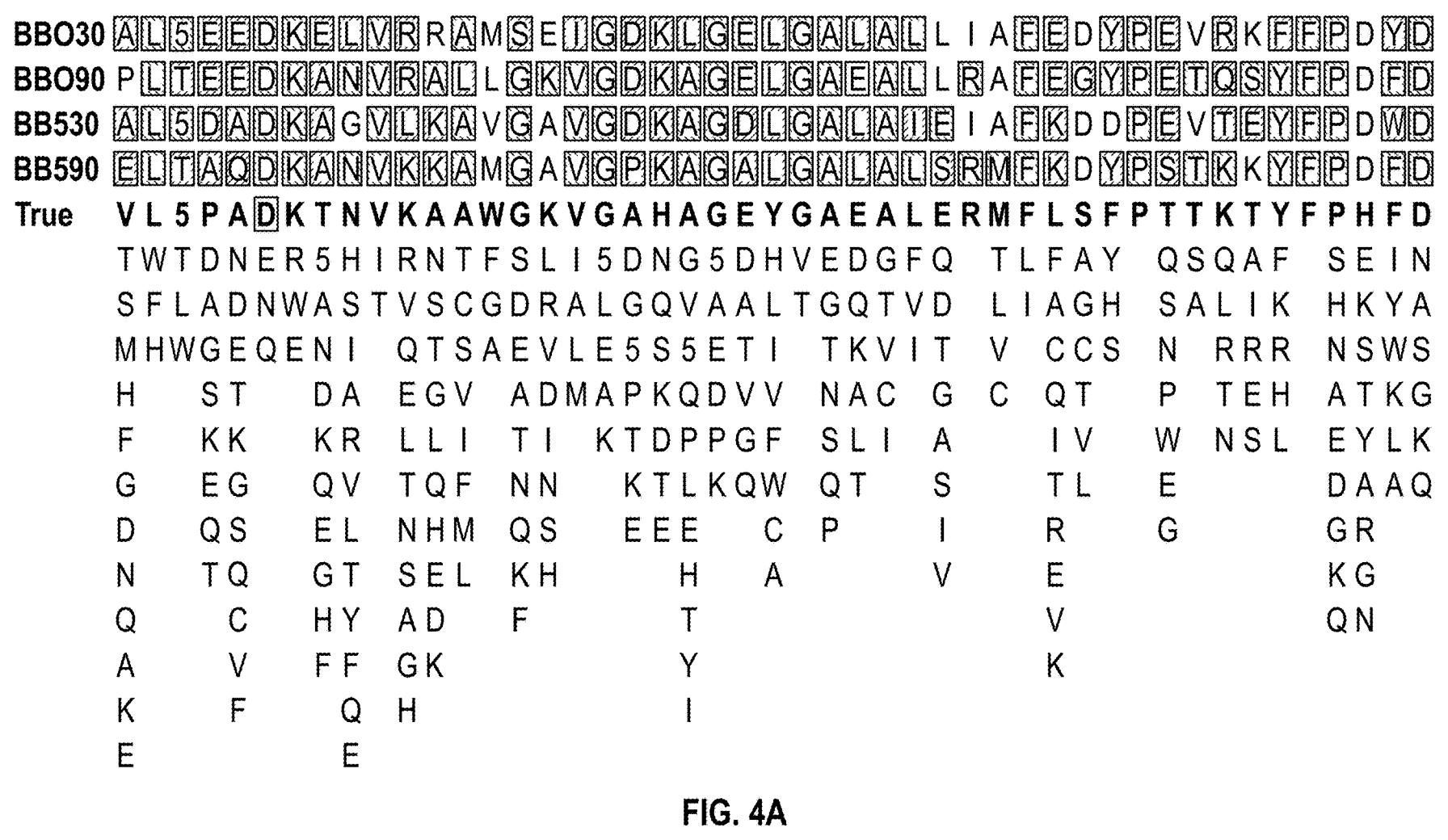
Figure 4C:
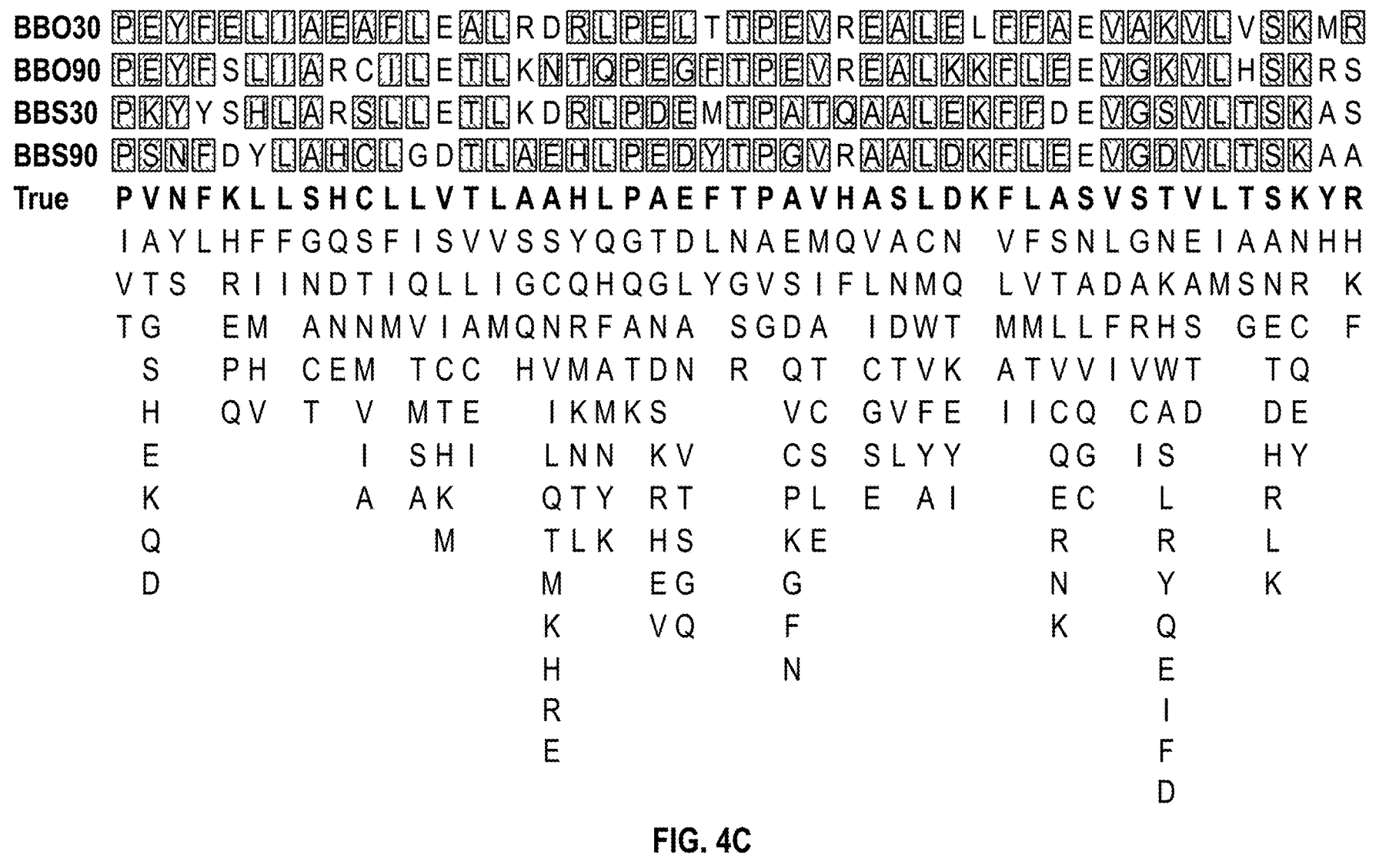

As shown at FIG. 4, the amino acid types that occur in at least one sequence (AA-homologous) are listed below the native sequence (red) of 1a3n for each position, and the predicted sequences by models BBO_ID30 (BB030), BBO_ID90 (BB090), BBS_ID30 (BBS30) and BBS_ID90 (BBS90) are shown above the native sequence.

FIG. 4 depicts sequence predictions by BBO_ID30 (BB030), BBO_ID90 (BB090), BBS_ID30 (BBS30) and BBS_ID90 (BBS90) model on human hemoglobin protein 1a3nB compare with true wild-type label. The amino acids shown below the true label row were possible amino acids at the corresponding position based on the sequences which are similar (p-value=0, twist=0) with 1a3nB calculated by FATCAT (Ye, Y. and Godzik, A. (2003) Flexible structure alignment by chaining aligned fragment pairs allowing twists. In, Bioinformatics). The boxes shaded with lines slanting from the top left to the bottom right of each box indicate an exactly correct prediction, and the boxes shaded with lines slanting from the bottom left to the top right of each box indicate that the prediction matches the possible amino acids.

The top-K recovery rates for BBO_ID90 model increased sharply from K=1 to K=2 and continued until K=5, for which the recovery rate was above 80% (FIG. 3). It is well-known that proteins can tolerate mutations on most of their sequence positions (see, e.g., FIG. 4). If the top-5 predictions correspond to those mutations that will not affect the protein stability significantly, then an effective sequence recover rate would be more than 80%. In most cases, residues similar in physical or chemical properties to the native residues were selected as the top-K predictions. This was further shown from the case study on deoxy human hemoglobin (FIG. 4). The soft recovery rate when taking into account of homologous sequences could reach more than 80%. It was hypothesized that a decent number of the predictions herein, although differing from the native sequences, may stabilize the given structure similarly or even more than the native sequences.

Table 2 depicts the average recovery rate of different models. The overall recovery rates of models BBO_ID30 and BBO_ID90 were tested on the dataset ID30TS (237000 amino acid residues) and ID90TS (990469 amino acid residues). The recovery rate of Wang et al.'s model was from five-fold cross-validation trained on a dataset consisting of 10173 protein chains with sequence identity lower than 30%. The overall recovery rate of SPIN and SPIN2 was from 10-fold cross-validation trained on a dataset composed of 1532 non-redundant proteins. These models were also tested on a small test dataset TS50 (50 protein chains) except SPIN2 which was tested on a dataset consisting of 500 protein chains including TS50.

Therefore, a convolutional neural network (CNN) model was developed to address the inverse folding problem (IFP)—inferring the sequence of a protein given its three-dimensional structure. ProDCoNN (Protein Design with Convolutional Neural Networks), achieved superior performance compared to those of earlier studies.

The top-K recovery rates for BBO_ID90 model increased sharply from K=1 to K=2 and continued until K=5, for which the recovery rate was above 80% (FIG. 3). It is well-known that proteins can tolerate mutations on most of their sequence positions (see, e.g., FIG. 4). If the top-5 predictions correspond to those mutations that will not affect the protein stability significantly, then an effective sequence recover rate would be more than 80%. In most cases, residues similar in physical or chemical properties to the native residues were selected as the top-K predictions. This was further shown from the case study on deoxy human hemoglobin (FIG. 4). The soft recovery rate when taking into account of homologous sequences could reach more than 80%. It was hypothesized that a decent number of the predictions herein, although differing from the native sequences, may stabilize the given structure similarly or even more than the native sequences.

TABLE

| Table 2: Average Recovery Rate of Different Models | | | | |
| --- | --- | --- | --- | --- |
| Model | BBO_ID30 | BBO_ID90 | Wang's model | SPIN | SPIN2 |
| Overall recovery rate | 42.20% | 46.50% | 34.0% | 30.7% | 34.4% |
| Recovery rate on TS50 | 38.71% | 40.69% | 33.0% | 30.3% | NA |

Table 3 depicts the results of a case study, including the recovery rate (%) and soft recovery rate (%) of the predicted sequences of deoxy human hemoglobin (pdb id: 1a3n, chain A and B) by different models.

TABLE 3

| Case Study | | | | |
| --- | --- | --- | --- | --- |
| Model | BBO_ID30 | BBO_ID90 | BBS_ID30 | BBS_ID90 |
| 1a3nA recovery rate | 38.30% | 45.39% | 46.10% | 58.16% |
| 1a3nA soft recovery rate | 81.56% | 83.69% | 82.98% | 86.52% |
| 1a3nB recovery rate | 38.62% | 51.72% | 44.14% | 62.76% |
| 1a3nB soft recovery rate | 78.62% | 86.21% | 80.00% | 90.03% |

A box shaded with lines slanting from the top left to the bottom right of each box at FIG. 4 indicates an exactly correct prediction, and a box shaded with lines slanting from the bottom left to the top right of each box indicates that the predictions fall into the AA-homologous set. The soft recovery rate was defined as the proportion of predictions that fell into either native sequence or the AA-homologous set. The results are shown in Table 3, the BBO_ID90 model yielded 83.69% and 86.21% soft recovery rates for 1a3 nA and 1a3nB, respectively, which were significantly highly than the sequence recovery rates (45.39% and 51.72%) without taking into account of homologous sequences.

Example 8—Confusion Matrix

To further investigate whether some of the wrong predictions may actually be compatible with the native structures, a confusion matrix was plotted for BBO_ID90 model (FIG. 5). In FIG. 5, the y-axis represents true labels and x-axis indicates predicted labels. The numbers in each grid indicates the population for each amino acid being predicted as 20 amino acids and the color shows the corresponding probability. From FIG. 5, it can be seen that the model made significant errors on distinguishing similar residues. For example, the cell corresponding to valine (VAL) and isoleucine (ILE) were the two residues with the highest number of errors, followed by GLU vs LYS and ALA vs SER. The errors made were not symmetric in that there are more ILE predicted as VAL than VAL predicted as ILE. Investigation of these errors may help to design better models to further improve the performance.

Similar matrices were collected for BBO_ID30, BBS_ID30, and BBS_ID90.

Interestingly, the confusion matrix displayed significant similarity (p-value=0 using permutation test) with the well-known amino acid substation matrices (i.e. BLOSUM62 matrix). This indicated that the models described herein likely performed better than they appeared using the stringent criterion of predicting the exact native amino acid types.

Some models have had a relatively poor performance on residues with low abundance compared to other amino acid residue types, such as methionine (MET) and tryptophan (TRP). The proportion of MET was 1.7% in ID30TR. As the number of MET in training data ID90TR (the proportion is the same) increased, the precision and recall by BBO_ID90 model increased significantly (FIG. 2B).

A cell (x,y) in the confusion matrix shows the number of times residue type x were predicted to be residue type y. FIG. 6A and FIG. 6B depict a modified-confusion matrix for BBO_ID90 and BLOSUM62, respectively.

Figures 7A, 7B, 7C, 7D:
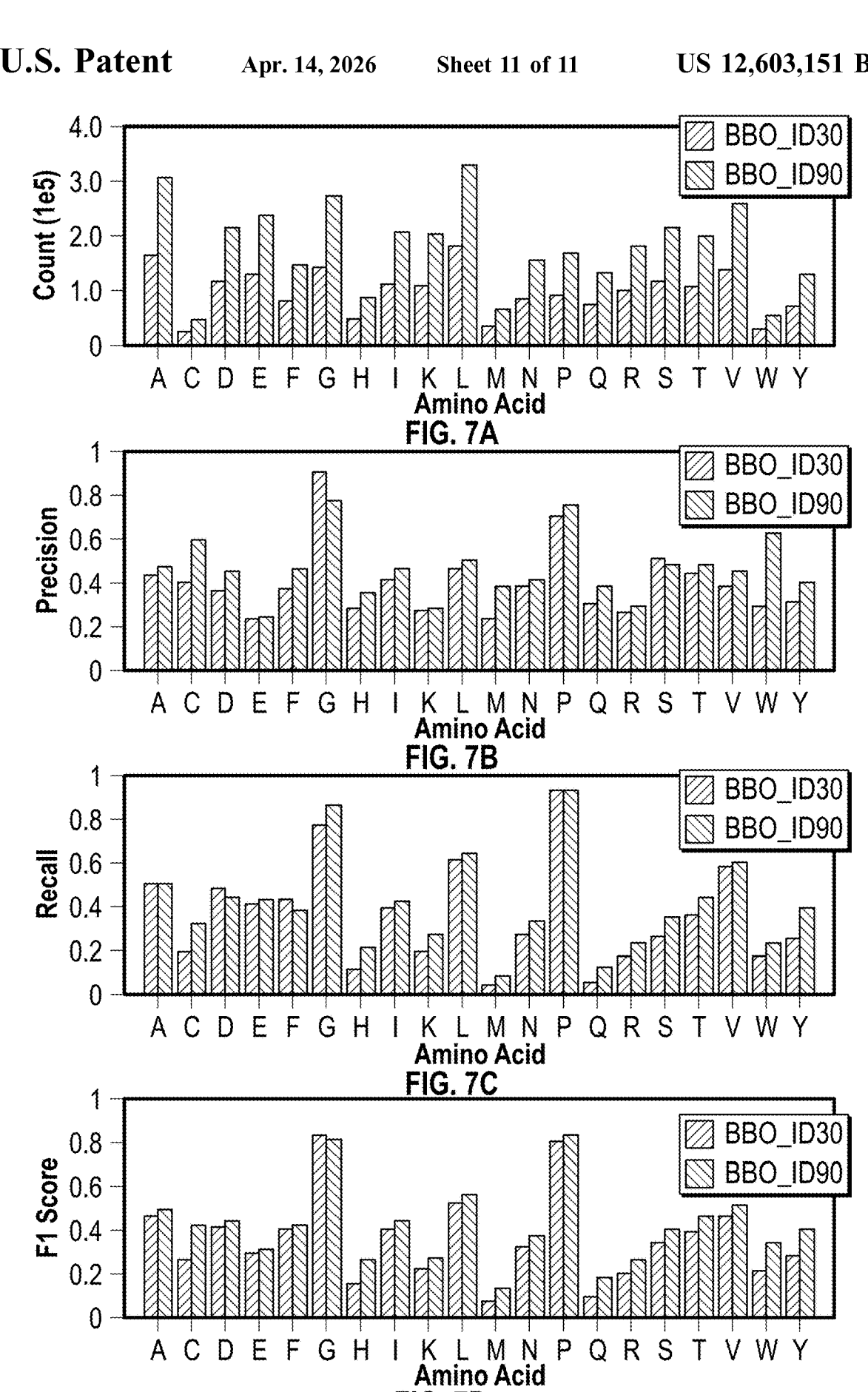
FIG. 7A depicts the count of each amino acid in an embodiment of a method.
FIG. 7B depicts the precision of different amino acids of the networks of an embodiment of a method.
FIG. 7C depicts the recall of different amino acids of the networks of an embodiment of a method.
FIG. 7D depicts the F1 score of different amino acids of the networks of an embodiment of a method.

FIG. 7A depicts the count of each amino acid in ID30TR and ID90TR). The precision, recall and F1 score of different amino acids of the networks BBO_ID30 and BBS_ID90 are depicted at FIG. 7B, FIG. 7C, and FIG. 7D, respectively.

The invention claimed is:

1. A method of predicting or designing a protein, the method comprising:

providing a protein comprising a target residue;

centering a gridded box on a selected atom of the target residue, wherein the gridded box has sides that are about 10 angstroms to about 30 angstroms in length;

collecting local structural information adjacent the selected atom and the target residue;

determining the target residue of the protein based on the local structural information, wherein the determining of the target residue comprises providing the local structural information as input data to a convolutional neural network; and modifying (i) the target residue to achieve a new function of the protein, or (ii) a designed protein to include the target residue to (a) achieve a new function of the designed protein, or (b) facilitate the folding of the designed protein into a known three-dimensional structure;

wherein the convolutional neural network has an architecture comprising—

(i) a layer comprising three parallel three dimensional convolution layers with rectified linear unit activation function, wherein (a) a first of the three parallel three dimensional convolution layers is configured to capture information on covalent bonds having lengths of from about 1.2 angstroms to about 1.8 angstroms, (b) a second of the three parallel three dimensional convolution layers is configured to recognize bond angles formed by two connected bonds, and (c) a third of the three parallel three dimensional convolution layers is configured to capture information on dihedral angles;

(ii) a 2×2×2 max pooling layer configured to produce an output of dimensions 9×9×9×80, (iii) a three dimensional convolution layer comprising 64 channels of 3×3×3 filter, and configured to detect secondary structure motifs, (iv) a 3×3×3 max pooling layer configured to produce an output of dimensions 3×3×3×64, (v) a flatten layer configured to convert an output of layer (iv) to a simple vector, (vi) a fully connected layer with rectified linear unit activation function, (vii) a dropout layer with a drop rate of 0.2, and (viii) a 20 dimensional activation layer.

2. The method of claim 1, wherein the selected atom of the target residue is a $C_\alpha$ atom of the target residue.

3. The method of claim 1, wherein the gridded box comprises a plurality of voxels, each voxel having a unit size of about 0.1 angstroms to about 2 angstroms by about 0.1 angstroms to about 2 angstroms by 0.1 angstroms to about 2 angstroms.

4. The method of claim 3, wherein the gridded box comprises about 4,000 to about 7,000 voxels.

5. The method of claim 1, wherein the providing of the protein comprises orienting the protein at a position wherein (i) a $C_\alpha$—C bond of the target residue aligns with or is arranged on an x-axis, and (ii) a $C_\alpha$—N bond of the target residue aligns with or is arranged in an x-y plane.

6. The method of claim 1, further comprising smoothing an input data comprising at least a portion of the local structural information by applying three dimensional truncated Gaussian functions with standard deviation $\sigma_x=\sigma_y=\sigma_z=r$, wherein r is equal to ±0.5 angstrom of a Van der Waals radius of an atom in a voxel of the gridded box.

7. The method of claim 6, wherein the Van der Waals radius for carbon, nitrogen, and oxygen is 0.7 angstroms, 0.65 angstroms, and 0.6 angstroms, respectively.

8. The method of claim 1, wherein the collecting of the local structural information comprises applying a backbone only model or a backbone with sequence model.

9. The method of claim 8, wherein the backbone only model has a recovery rate of at least 50%, a soft recovery rate of at least 80%, or a combination thereof.

10. The method of claim 8, wherein the backbone with sequence model has a recovery rate of at least 60%, a soft recovery rate of at least 85%, or a combination thereof.

* * * * *